(12) United States Patent
Hayashi

(10) Patent No.: US 7,951,526 B2
(45) Date of Patent: *May 31, 2011

(54) MODIFIED SILICA PARTICLES, AND PHOTOSENSITIVE COMPOSITION AND PHOTOSENSITIVE LITHOGRAPHIC PRINTING PLATE EACH CONTAINING THE PARTICLES

(75) Inventor: Koji Hayashi, Tatebayashi (JP)

(73) Assignee: Eastman Kodak Company, Rochester, NY (US)

( * ) Notice: Subject to any disclaimer, the term of this patent is extended or adjusted under 35 U.S.C. 154(b) by 527 days.

This patent is subject to a terminal disclaimer.

(21) Appl. No.: 11/913,727

(22) PCT Filed: May 8, 2006

(86) PCT No.: PCT/JP2006/309610
§ 371 (c)(1),
(2), (4) Date: Nov. 6, 2007

(87) PCT Pub. No.: WO2006/121172
PCT Pub. Date: Nov. 16, 2006

(65) Prior Publication Data
US 2009/0092923 A1    Apr. 9, 2009

(30) Foreign Application Priority Data

May 12, 2005 (JP) .................................. 2005-140411

(51) Int. Cl.
*G03F 7/004* (2006.01)
*G03F 7/24* (2006.01)

(52) U.S. Cl. .................. 430/281.1; 430/270.1; 430/302; 101/453

(58) Field of Classification Search ............... 430/270.1, 430/302
See application file for complete search history.

(56) References Cited

U.S. PATENT DOCUMENTS

| | | | | |
|---|---|---|---|---|
| 4,756,993 | A | * | 7/1988 | Kitatani et al. ................. 430/69 |
| 6,114,083 | A | * | 9/2000 | Kawamura et al. ......... 430/270.1 |
| 6,160,067 | A | | 12/2000 | Eriyama et al. |
| 6,534,235 | B1 | * | 3/2003 | Hanabata et al. ............. 430/191 |
| 2008/0280228 | A1 | * | 11/2008 | Hayashi et al. ............. 430/272.1 |

FOREIGN PATENT DOCUMENTS

JP        2002166670  A   *   6/2002

OTHER PUBLICATIONS

JP Abstract 05-269365 (Oct. 19, 1993).
JP Abstract 11-060235 (Mar. 2, 1999).
JP Abstract 2003-137530 (May 14, 2003).

* cited by examiner

*Primary Examiner* — Cynthia H Kelly
*Assistant Examiner* — Chanceity N Robinson
(74) *Attorney, Agent, or Firm* — J. Lanny Tucker

(57) ABSTRACT

Adhesion between a photosensitive layer and a substrate after the exposure of a photosensitive lithographic printing plate containing the photosensitive layer and substrate is achicbed by incorporating modified silica particles into the photosensitive layer. The surface of the silica paricles is modified by an organic compound having at least one ethylenically unsaturated group, at least one hydrophilic moiety, and at least one silyloxy group.

20 Claims, 1 Drawing Sheet

MODIFIED SILICA PARTICLES, AND PHOTOSENSITIVE COMPOSITION AND PHOTOSENSITIVE LITHOGRAPHIC PRINTING PLATE EACH CONTAINING THE PARTICLES

TECHNICAL FIELD

The present invention relates to modified silica particles having modified surfaces and to a photosensitive composition and a photosensitive lithographic printing plate each containing the modified silica particles.

BACKGROUND ART

With the progress of a computer image-processing technique, a method of directly writing images on a photosensitive layer, by light irradiation corresponding to digital signals, has recently been developed. An intense interest has been shown toward a computer-to-plate (CTP) system in which images are directly formed on a photosensitive lithographic printing plate, without outputting the images onto a silver-salt mask film, by employing said method for a lithographic printing plate precursor.

A negative photosensitive lithographic printing plate for a CTP system includes, for example, a so-called photopolymer type photosensitive lithographic printing plate in which a photosensitive layer, made mainly of a photocurable resin, is formed on a substrate. In the photopolymer type photosensitive lithographic printing plate, a photopolymerization initiator contained in the photosensitive layer is excited, on exposure, to form a radical whereby the photocurable resin is crosslinked and insolubilized to form an image.

By the way, when the crosslinking reaction of the photocurable resin proceeds, the photosensitive layer is necessarily contracted. The contraction may decrease the adhesion between the substrate and the photosensitive layer of the photosensitive lithographic printing plate thereby to deteriorate printing characteristics. Therefore, as described in Japanese Unexamined Patent Publication (Kokai) No. 11-143082, there is proposed a technique in which fillers such as silica particles are incorporated into the photosensitive layer thereby to increase the strength the photosensitive layer and to reduce the contraction of the photosensitive layer.

However, even when these fillers are used, it is still difficult to sufficiently secure adhesion between the photosensitive layer and the substrate, thus lowering the run length of the photosensitive lithographic printing plate.

DISCLOSURE OF THE INVENTION

Under these circumstances, the present invention has been made. An object of the present invention is to provide a novel filler which suppresses or reduces self-contraction on crosslinking the photosensitive layer, and to satisfactorily maintain adhesion between the photosensitive layer and the substrate after the exposure of the photosensitive lithographic printing plate.

The object of the present invention is achieved by modified silica particles, the surfaces of which being modified by an organic compound having at least one ethylenically unsaturated group, at least one hydrophilic moiety and at least one silyloxy group.

The hydrophilic moiety is preferably a polyoxyalkylene chain, and the ethylenically unsaturated group and the silyloxy group are preferably located at both ends of the molecular chain of the organic compound.

The organic compound is preferably represented by the following formula:

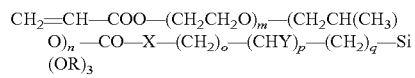

wherein
R represents a $C_1$-$C_6$ alkyl group,
X represents a divalent organic group selected from
—$CH_2$—,
—O—, —S— and —NZ— (Z represents H or a $C_1$-$C_6$ alkyl group),
Y represents a $C_1$-$C_6$ alkyl group or a halogen atom,
m represents an integer of 0 to 100,
n represents an integer of 0 to 100,
provided that m+n represents 1 or more,
O represents an integer of 0 to 10,
p represents an integer of 0 to 5, and
q represents an integer of 0 to 10,
provided that o+q represents 1 or more.

The modified silica particles of the present invention can be preferably incorporated into a photosensitive composition containing a photopolymerizable compound as a filler. As a photosensitive layer on a substrate of a photosensitive lithographic printing plate, the photosensitive composition can be preferably used.

According to the modified silica particles of the present invention, since contraction on crosslinking of a photosensitive composition containing the same can be suppressed or reduced, adhesion between the photosensitive layer and the substrate can be satisfactorily maintained after the exposure of a photosensitive lithographic printing plate comprising a substrate and a photosensitive layer made of the photosensitive composition formed on the substrate. Therefore, the run length of the photosensitive lithographic printing plate can be improved.

BEST MODE FOR CARRYING OUT THE INVENTION

Figure 1:
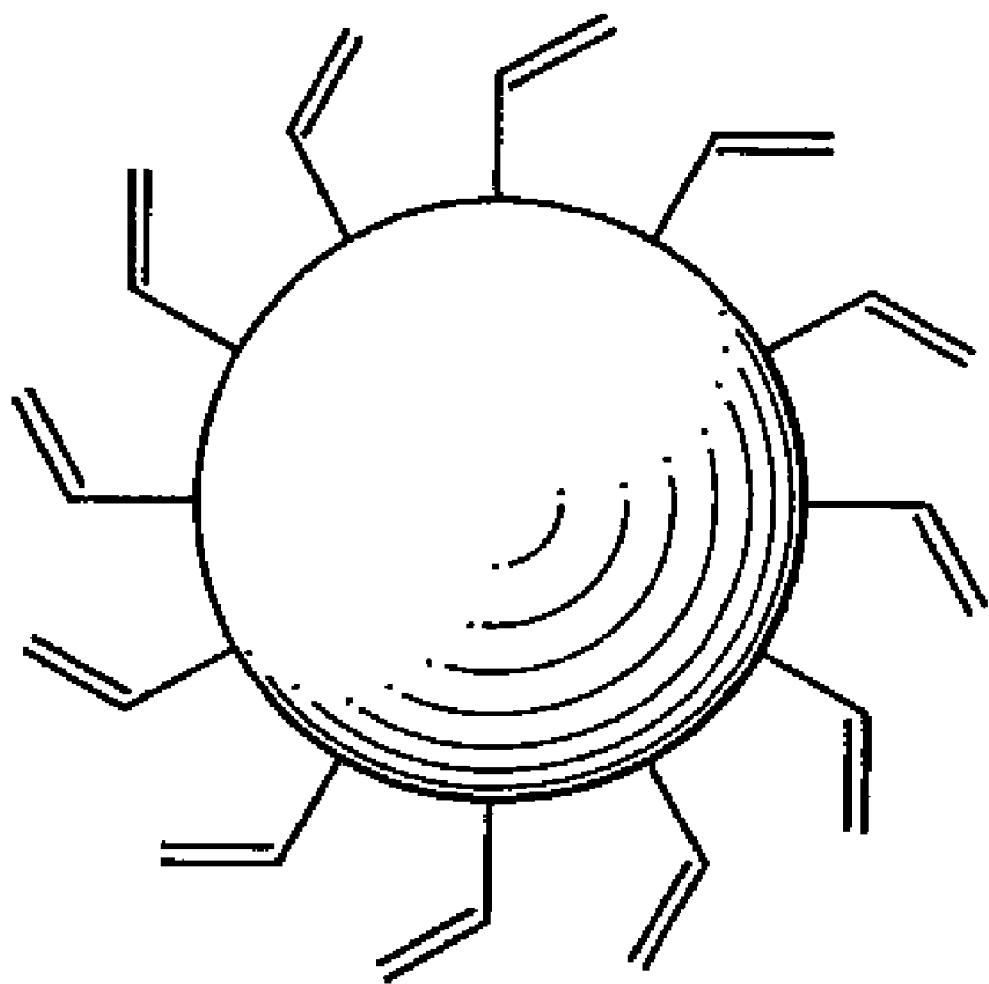
FIG. 1 is a schematic diagram showing surface modification of modified silica particles of the present invention.

Silica particles, the surface of which is to be modified in the present invention, are commonly used in this technical field and contain silicon oxide ($SiO_2$) as a main component. The particle size of the silica particles is usually within a range from 1 to 1000 nm, preferably from 1 to 500 nm, and more preferably from 1 to 100 nm. The silica particles are commercially available and examples thereof include Snowtex OL (aqueous solution containing 20% colloidal silica having a particle size of 45 nm) and MEK-ST (methyl ethyl ketone solution containing 30% colloidal silica having a particle size of 10 to 20 nm) manufactured by NISSAN CHEMICAL INDUSTRIES, LTD., AEROSIL 130 (silica having a particle size of 16 nm) manufactured by Nippon Aerosil Co., Ltd., and Mizukasil P-527U (silica having a particle size of 60 nm) manufactured by MIZUSAWA INDUSTRIAL CHEMICALS, LTD.

In silica particles, types such as fumed silica, precipitated silica and colloidal silica are available. Among these types, colloidal silica is preferably used.

In the present invention, the surfaces of the silica particles are modified by an organic compound having at least one ethylenically unsaturated group, at least one hydrophilic moiety and at least one silyloxy group, to give modified silica particles.

An ethylenically unsaturated group is required to secure reactivity with a photopolymerizable compound described hereinafter. A silyloxy group is required to secure bonding with the silica particles. The ethylenically unsaturated group and the silyloxy group are preferably located at both ends of the molecular chain of the organic compound. In this case, the hydrophilic moiety is present between the ethylenically unsaturated group and the silyloxy group.

The hydrophilic moiety is not specifically limited, but is preferably a polyoxyalkylene chain. The alkylene chain may be a polyethylene chain, a polypropylene chain or a polyethylene-polyoxypropylene chain. Particularly, the polyethylene chain is preferable.

Specifically, the organic compound is preferably represented by the following formula:

$$CH_2=CH-COO-(CH_2CH_2O)_m-(CH_2CH(CH_3)O)_n-CO-X-(CH_2)_o-(CHY)_p-(CH_2)_q-Si(OR)_3$$

wherein

R represents a $C_1$-$C_6$ alkyl group, and preferably a methyl group or an ethyl group, X represents a divalent organic group selected from —$CH_2$—, —O—, —S— and —NZ— (Z represents H or a $C_1$-$C_6$ alkyl group), and preferably NH, Y represents a $C_1$-$C_6$ alkyl group or a halogen atom, and preferably a methyl group or a fluorine atom, m represents an integer of 0 to 100, and preferably an integer of 1 to 50, n represents an integer of 0 to 100, and preferably an integer of 0 to 20, provided that m+n represents 1 or more, O represents an integer of 0 to 10, and preferably an integer of 1 to 10, p represents an integer of 0 to 5, and preferably an integer of 0 to 2, and q represents an integer of 0 to 10, and preferably an integer of 1 to 10, provided that o+q represents 1 or more, and preferably 2 or more.

When the organic compound of the above formula is reacted with the silica particles, a silyloxy group (—Si(OR)$_3$) is reacted with a hydroxyl group on the surface of silica to form a covalent bond and, therefore, the surface of the silica particles is modified as shown in FIG. 1. Ethylenically unsaturation bonded to the surface of silica serves as a reactive site with a photopolymerizable compound described hereinafter.

The organic compound is obtained, for example, by reacting polyethylene glycol acrylate with 3-isocyanatepropyltriethoxysilane. The organic compound obtained by the reaction has the following structure.

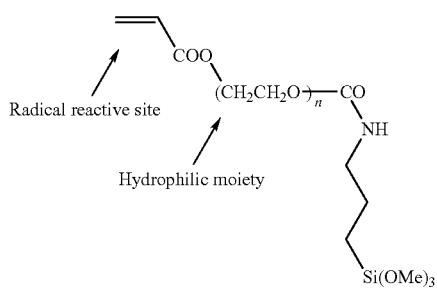

Surface modification of the silica particles by using the organic compound can be conducted by a common technique in this technical field and, for example, by a technique of contacting them for a predetermined time. A modification rate of the surface of the silica particles is usually within a range from 50 to 99%, and preferably from 80 to 99%. The modification rate of the surface of the silica particles can be controlled by adjusting a weight ratio of the silica particles to the organic compound.

As the organic compound used in the present invention has at least one ethylenically unsaturated bond, the photosensitive composition containing the silica particles modified by the organic compound and the photopolymerizable compound causes less contraction on curing and therefore adhesion with the substrate scarcely decreases. Therefore, in the photosensitive lithographic printing plate comprising a substrate and the photosensitive photosensitive layer made of the composition formed on the substrate, good integration between the substrate and the photosensitive layer can be maintained by crosslinking of the photopolymerizable compound in the photosensitive layer. As a result, adhesion between the photosensitive layer and the substrate is good. If the organic compound has no ethylenically unsaturated bond, the adhesion between the photosensitive layer and the substrate decreases.

The photosensitive composition and the photosensitive lithographic printing plate of the present invention will now be described in more detail. The photosensitive composition of the present invention essentially contains modified silica particles and a photopolymerizable compound.

[Photopolymerizable Compound]

The photopolymerizable compound contained in the photosensitive composition of the present invention is not specifically limited, but is preferably a compound having an addition-polymerizable ethylenically unsaturated bond. The compound can be optionally selected from compounds having at least one, and preferably two or more ethylenically unsaturated double bond groups at the end. The compound has chemical forms, for example, monomer and prepolymer such as dimer, trimer and oligomer, or mixtures thereof and copolymers thereof. Examples of the monomer and the copolymer thereof include an ester of an unsaturated carboxylic acid (for example, acrylic acid, methacrylic acid, itaconic acid, crotonic acid, isocrotonic acid, maleic acid, etc.) and an aliphatic polyhydric alcohol compound, and an amide of an unsaturated carboxylic acid and an aliphatic polyhydric amine compound.

Specific examples of the ester of the aliphatic polyhydric alcohol compound and the carboxylic acid include acrylate esters such as ethylene glycol diacrylate, triethylene glycol diacrylate, 1,3-butanediol diacrylate, tetramethylene glycol diacrylate, propyleneglycol diacrylate, neopentyl glycol diacrylate, trimethylolpropane triacrylate, trimethylolpropanetri(acryloyloxypropyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol pentaacrylate, dipentaerythrito hexaacrylate, sorbitol triacrylate, sorbitol tetraacrylate, sorbitol pentaacrylate, sorbitol hexaacrylate, tri (acroyloxyethyl) isocyanurate and polyester acrylate oligomer.

Examples of methacrylate esters include tetramethylene glycol dimethacrylate, triethylene glycol dimethacrylate, neopentylglycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, dipentaerythritol pentamethacrylate, sorbitol trimethacrylate, sorbitol tetramethacrylate, bis[p-(3-methacryloxy-2-hydroxypropoxy)phenyl]dimethylmethane and bis-[p-(methacryloxyethoxy)phenyl]dimethylmethane.

Examples of itaconate esters include ethylene glycol diitaconate, propylene glycol diitaconate, 1,3-butanediol diitaconate, 1,4-butanediol diitaconate, tetramethylene glycol diitaconate, pentaerythritol diitaconate and sorbitolte traitaconate.

Examples of crotonate esters include ethylene glycol dicrotonate, tetramethylene glycol dicrotonate, pentaerythritol dicrotonate and sorbitol tetradicrotonate.

Examples of isocrotonate ester include ethylene glycol diisocrotonate, pentaerythritol diisocrotonate and sorbitol tetraisocrotonate.

Examples of maleate esters include ethylene glycol dimaleate, triethylene glycol dimaleate, pentaerythritol dimaleate and sorbitol tetramaleate. Furthermore, mixtures of the above ester monomers can be exemplified.

Specific examples of the amide of the aliphatic polyvalent amine compound and the unsaturated carboxylic acid include methylenebis-acrylamide, methylenebis-methacrylamide, 1,6-hexamethylenebis-acrylamide, 1,6-hexamethylenebis-methacrylamide, diethylenetriaminetrisacrylamide, xylylenebisacrylamide and xylylenebismethacrylamide.

The other examples include a vinylurethane compound having two or more polymerizable vinyl groups in a molecule, which is obtained by adding the ester of the unsaturated carboxylic acid and the aliphatic polyhydric alcohol compound, or a vinyl monomer having a hydroxyl group represented by the following general formula (A) or (B) to a polyisocyanate compound having two or more isocyanate groups in a molecule such as hexamethylene diisocyanate. The compound to be reacted with an isocyanate group preferably has an amino group and an imino group in the molecule.

$CH_2=C(Q^1)COOCH_2CH(Q^2)OH$  (A)

wherein $Q^1$ and $Q^2$ independently represents H or $CH_3$

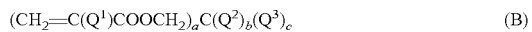

$(CH_2=C(Q^1)COOCH_2)_aC(Q^2)_b(Q^3)_c$  (B)

wherein $Q^1$ and $Q^2$ independently represents H or $CH_3$, $Q^3$ represents —$CH_2OH$, and a and c each independently represents an integer of 1 to 3 and b represents an integer of 0 or 1 or 2, provided that a+b+c represents 4

Also there can be exemplified polyfunctional acrylates and methacrylates, for example, urethane acrylates described in Japanese Unexamined Patent Publication (Kokai) No. 51-37193, polyester acrylates described in Japanese Unexamined Patent Publication (Kokai) No. 48-64183, Japanese Examined Patent Publication (Kokoku) No. 49-43191 and Japanese Examined Patent Publication (Kokoku) No. 52-30490, and epoxy acrylates obtained by reacting an epoxy resin with (meth)acrylic acid. Furthermore, there can be used photocurable monomers and oligomers described in Journal of Japanese Adhesion Society, Vol. 20, No. 7, pp. 300-308 (1984).

Specific examples thereof include NK OLIGO U-4HA, U-4H, U-6HA, U-108A, U-1084A, U-200AX, U-122A, U-340A, U-324A and UA-100 (which are manufactured by Shin-Nakamura Chemical Corporation); UA-306H, AI-600, UA-101T, UA-101I, UA-306T and UA-306I (which are manufactured by Kyoeisha Oil and Fats Chemical Ind. Co., Ltd.); and ART RESIN UN-9200A, UN-3320HA, UN-3320HB, UN-3320HC, SH-380G, SH-500, SH-9832 (which are manufactured by Negami Chemical Industrial Co., Ltd.).

The amount of these photopolymerizable compounds is preferably within a range from 5 to 90% by weight, and more preferably from 10 to 80% by weight, based on the entire components of the photosensitive composition.

It is preferred that the photosensitive composition of the present invention further contains, in addition to the modified silica particles and the photopolymerizable compound, (a) an infrared absorber,
(b) a photopolymerization initiator, and
(c) a binder resin.

[Infrared Absorber]

The infrared absorber, which can be incorporated into the photosensitive composition of the present invention, is a material having a maximum absorption wavelength in a near infrared or infrared range, for example, a maximum absorption wavelength in a range from 760 nm to 1200 nm. Examples of the material include various pigments or dyes.

The pigments used in the present invention are commercially available pigments described, for example, in "Color Index Handbook, "Latest Pigment Handbook" (edited by Nihon Pigment Technique Society, published in 1977), "Latest Pigment Application Technique" (published by CMC in 1986), and "Printing Ink Technique" (published by CMC in 1984). Applicable types of pigments include black, yellow, orange, brown, red, violet, blue and green pigments, fluorescent pigments and polymer-grafted dyes. For example, there can be used insoluble azo pigments, azo lake pigments, condensed azo pigments, chelated azo pigments, phthalocyanine pigments, anthraquinone pigments, perylene and perinone pigments, thiomindigo pigments, guinacridone pigments, dioxazine pigments, isoindolinone pigments, quinophthalone pigments, lake pigments, azine pigments, nitroso pigments, nitro pigments, natural pigments, fluorescent pigments, inorganic pigments and carbon black.

Among these pigments, carbon black is preferably used as a material which efficiently absorbs light in a near infrared or infrared range and is also economically excellent. As the carbon black, grafted carbon blacks having various functional groups, which are excellent in dispersibility, are commercially available and examples thereof include those described on page 167 of "The Carbon Black, Handbook, 3rd edition" (edited by the Carbon Black Society of Japan and issued in 1995" and those described in page 111 of "Characteristics, Optimum Blending and Applied Technique of Carbon Black" (edited by Technical Information Society in 1997), all of which are preferably used in the present invention.

These pigments may be used without surface treatment, or may be used after subjected to a surface treatment. As a method of surface treatment, there can be contemplated a method of surface-coating a resin or a wax, a method of attaching a surfactant, and a method of binding a reactive substance (e.g. silane coupling agent, epoxy compound, polyisocyanate etc.) to the surface of a pigment. The above-mentioned surface treating methods are described in "Property and Application of Metal Soap" (Saiwai Shobou), "Printing Ink Technique" (published by CMC in 1984) and "Latest Pigment Application Technique" (published by CMC in 1986).

The particle size of these pigments is preferably in a range from 0.01 to 15 µm, and more preferably from 0.01 to 5 µm.

The dyes used in the present invention are conventionally known commercially available dyes described, for example, in "Dye Handbook" (edited by the Association of Organic Synthesis Chemistry, published in 1970), "Handbook of Color Material Engineering" (edited by the Japan Society of Color Material, Asakura Shoten K. K., published in 1989), "Technologies and Markets of Industrial Pigments" (published by CMC in 1983), and "Chemical Handbook, Applied Chemistry Edition" (edited by The Chemical Society of Japan, Maruzen Shoten K. K., published in 1986). Specific examples of the dyes include azo dyes, azo dyes in the form of metal complex salts, pyrazolone azo dyes, anthraquinone dyes, phthalocyanine dyes, carbonium dyes, quinonimine dyes, methine dyes, cyanine dyes, indigo dyes, quinoline dyes, nitro-based dyes, xanthene-based dyes, thiazine-based dyes, azine dyes, and oxazine dyes.

The dyes capable of efficiently absorbing near-infrared or infrared light are described, for example, in EP-A-0,823,327, U.S. Pat. No. 4,973,572 and U.S. Pat. No. 5,208,135. Specific examples thereof include cyanine dyes, hemicyanine dyes, streptocyanine dyes, methine dyes, polymethine dyes, allylmethine dyes, pyrylium salts, oxonol dyes, anthraquinone-based dyes, porphyrin dyes, azo dyes, croconium dyes, triallylamine-based compounds, thiazolium salts, oxazolium salts, indocyanine compounds, indotricarbocyanine dyes, oxatricarbocyanine dyes, phthalocyanine dyes, thiocyanine dyes, thiatricarbocyanine dyes, merocyanine dyes, naphthalocyanine dyes, polyaniline dyes, polypyrrole derivatives, polythiophene derivatives, chalcogenopyryloallylidene compounds, bis(chalcogenopyrylo)polymethine dyes, oxy indolizine derivatives, pyrazoline azo dyes, oxazine dyes, naphthoquinone dyes, squalirium dyes, arylbenzo(thio)pyridinium salts, trimethinethiapyrylium salts, pyrylium-based compounds, pentamethinethiopyrylium salts and infrared absorbing dyes. Furthermore, ADS-830A and ADS-106 manufactured by Americal Dye Source, Inc. can also be used.

Among these dyes, a near-infrared absorbing cationic dye represented by the following general formula:

D$^+$A$^-$ wherein D$^+$ represents a cationic dye having an absorption in a near infrared range and A$^-$ represents an anion, is preferable as the infrared absorber because it enables the below described organic boron compound to efficiently exert a polymerization function.

Examples of the cationic dye having an absorption in a near infrared range include cyanine-based dyes, triarylmethane-based dyes, ammonium-based dyes and diimmonium-based dyes, each having an absorption in a near infrared range. Specific examples of the cationic dye having an absorption in a near infrared range include the followings.

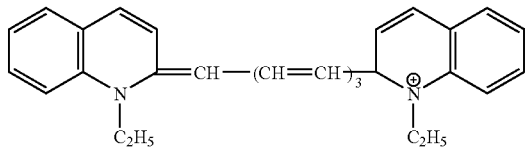

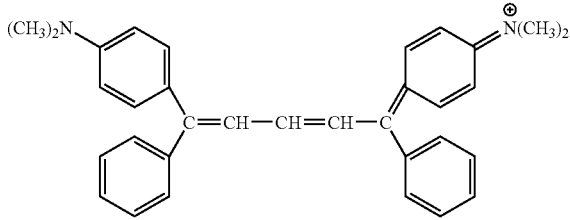

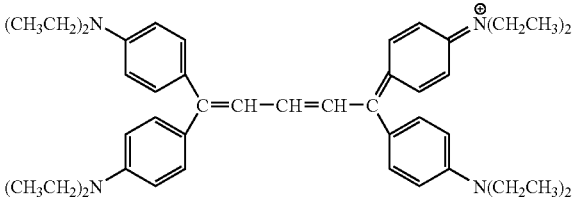

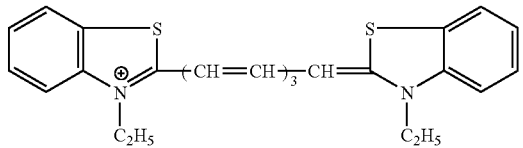

-continued
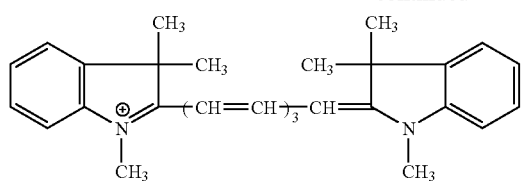
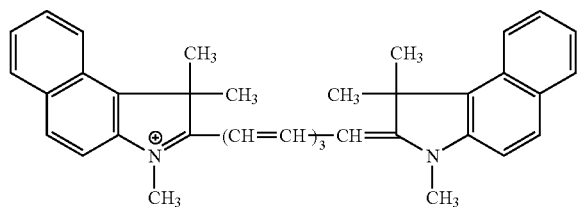
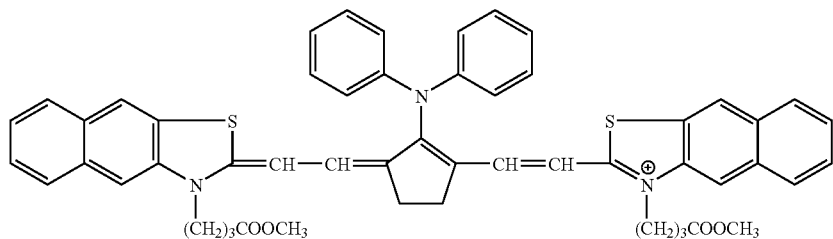
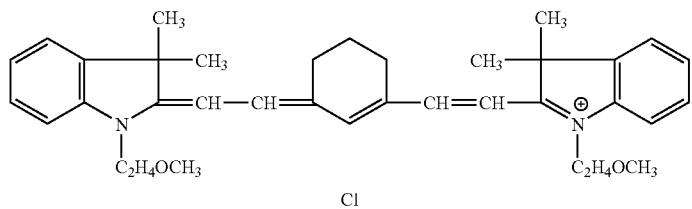
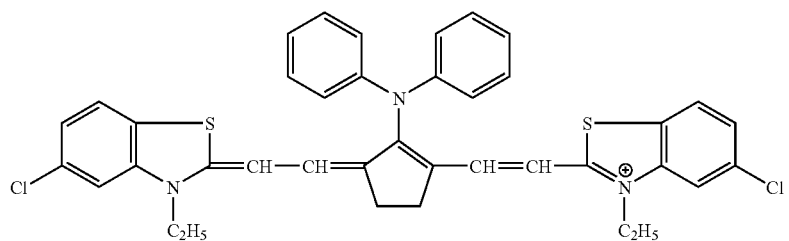
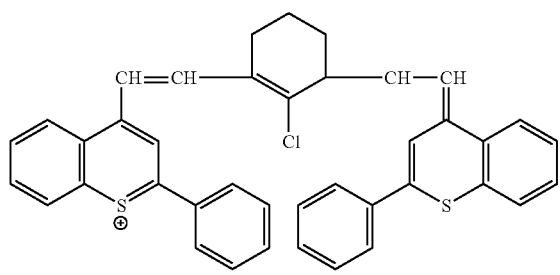

-continued

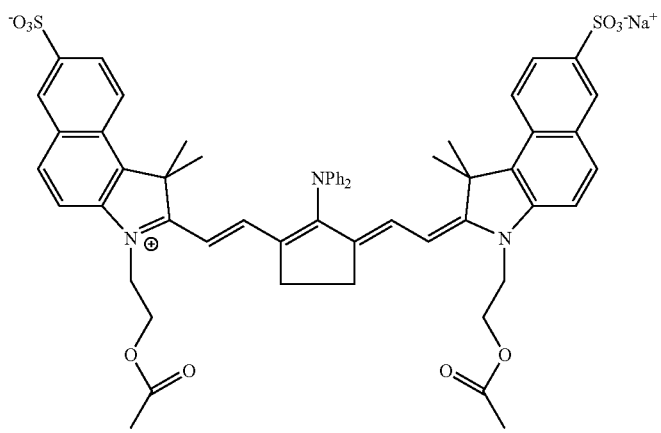

(A)

Examples of the anion include halogen anion, $ClO_4^-$, $PF_6^-$, $BF_4^-$, $SbF_6^-$, $CH_3SO_3^-$, $CF_3SO_3^-$, $C_6H_5SO_3^-$, $CH_3C_6H_4SO_3^-$, $HOC_6H_4SO_3^-$, $ClC_6H_4SO_3^-$, and boron anion represented by the following formula (3). The boron anion is preferably a triphenyl n-butylboron anion or a trinaphthyl n-butylboron anion.

(3)

wherein $R^1$, $R^2$, $R^3$ and $R^4$ each independently represents an alkyl group, an aryl group, an alkaryl group, an allyl group, an aralkyl group, an alkenyl group, an alkynyl group, an alicyclic group, or a saturated or unsaturated heterocyclic group, and at last one of $R^1$, $R^2$, $R^3$ and $R^4$ is an alkyl group having 1 to 8 carbon atoms.

In the present invention, specific examples of the cyanine dye, which can be preferably used, also include those described in paragraph numbers [0017] to [0019] of the specification of Japanese Unexamined Patent Publication (Kokai) No. 2001-133969, and those described in paragraph numbers [0032] to [0035] of the specification of Japanese Unexamined Patent Publication (Kokai) No. 2002-40638.

The infrared absorber is used in the following manner. That is, at least one proper pigment or dye capable of absorbing a specific wavelength of a light source described hereinafter is selected from the above pigments or dyes and then added to the photosensitive composition.

When the pigment is used as the infrared absorber, the content of the pigment is preferably within a range from 0.5 to 15% by weight, and particularly preferably from 1 to 10% by weight, based on the entire solid content of the photosensitive composition. When the content of the pigment is less than 0.5% by weight, infrared ray is not sufficiently absorbed. On the other hand, when the content of the pigment is more than 15% by weight, an excess quantity of heat tends to be generated, and therefore it is not preferred.

When the dye is used as the infrared absorber, the content of the dye is preferably within a range from 0.5 to 15% by weight, and particularly preferably from 1 to 10% by weight, based on the entire solid content of the photosensitive composition. When the content of the dye is less than 0.5% by weight, infrared light is not sufficiently absorbed. On the other hand, when the content of the dye is more than 15% by weight, absorption of infrared light is substantially saturated and the effect of the addition of the dye may not increase, and therefore it is not preferred.

[Photopolymerization Initiator]

As a photopolymerization initiator, it is possible to use various photopolymerization initiators known from patent documents and non-patent documents alone or in combination (photopolymerization initiation system) after appropriately selecting according to the wavelength of a light source to be used. In the present invention, the photopolymerization initiators to be used alone or in combination are merely referred to as a "photopolymerization initiator".

As the photopolymerization initiator, organic boron compounds, onium salts and triazine-based compounds are preferable. These photopolymerization initiators may be used alone or in combination.

The organic boron compound can exert a function as a polymerization initiator by using in combination with the above infrared absorber. The organic boron compound is preferably an ammonium salt of a quaternary boron anion, which is represented by the following formula (2):

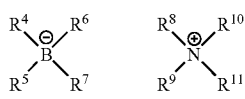

(2)

wherein $R^4$, $R^5$, $R^6$ and $R^7$ each independently represents an alkyl group, an aryl group, an alkaryl group, an allyl group, aralkyl group, an alkenyl group, an alkynyl group, an alicyclic group, or a saturated or unsaturated heterocyclic group, at least one of $R^1$, $R^2$, $R^3$ and $R^4$ is an alkyl group having 1 to 8 carbon atoms, and $R^8$, $R^9$, $R^{10}$ and $R^{11}$ each independently represents a hydrogen atom, an alkyl group, an aryl group, an allyl group, an alkaryl group, an aralkyl group, an alkenyl group, an alkynyl group, an alicyclic group, or a saturated or unsaturated heterocyclic group.

Among these, tetra n-butylammoniumtriphenylboron, tetra n-butylammoniumtrinaphthylboron, tetra n-butylammoniumtri(p-t-butylphenyl)boron, tetramethylammonium n-butyltriphenylboron, tetramethylammonium n-butyltrinaphthylboron, tetramethylammonium n-octyltriphenylboron, tetramethylammonium n-octyltrinaphthylboron, tetraethylammonium n-butyltriphenylboron, tetraethylammonium n-butyltrinaphthylboron, trimethylhydrogenammonium n-butyltriphenylboron, triethylhydrogenammonium n-butyltriphenylboron, tetrahydrogenammonium n-butyltriphenylboron, tetramethylammoniumtetra n-butylboron and tetraethylammoniumtetra n-butylboron can be preferably used because a polymerization function are efficiently exerted.

The organic boron compound can exert a function as a polymerization initiator by using in combination with the above infrared absorber (for example, $D^+A^-$) in case of generating a radical (R·) by irradiation with infrared ray, as shown in the following scheme (5):

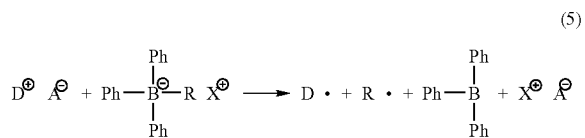

(5)

wherein Ph represents a phenyl group, R represents can alkyl group having 1 to 8 carbon atoms, and $X^+$ represents an ammonium ion.

The content of the organic boron compound is preferably within a range from 0.1 to 15% by weight, and particularly preferably from 0.5 to 7% by weight, based on the solid content of the photosensitive layer. When the content of the organic boron compound is less than 0.1% by weight, an insufficient polymerization reaction leads to poor curing and the resulting negative photosensitive lithographic printing plate has a weak image area. On the other hand, when the content of the organic boron compound is more than 15% by weight, the polymerization reaction does not efficiently arise. If necessary, at least two organic boron compounds (B) may be used in combination.

The onium salt is a salt comprising a cation having at least one onium ion atom in the molecule, and an anion. Examples of the onium ion atom in the onium salt include $S^+$ atom in sulfonium, $I^+$ atom in iodonium, $N^+$ in ammonium, $P^+$ atom in phosphonium, and $N^{2+}$ in diazonium. Among these onium ion atoms, $S^+$, $I^+$ and $N^{2+}$ atoms are preferable. Examples of the structure of the onium salt include triphenylsulfonium, diphenyliodonium, diphenyldiazonium, and derivatives obtained by introducing an alkyl group and an aryl group into the benzene ring of these compounds, and derivatives obtained by introducing an alkyl group and an aryl group into the benzene ring of these compounds.

Examples of the anion of the onium salt include halogen anion, $ClO_4^-$, $PF_6^-$, $BF_4^-$, $SbF_6^-$, $CH_3SO_3^-$, $CF_3SO_3^-$, $C_6H_5SO_3^-$, $CH_3C_6H_4SO_3^-$, $HOC_6H_4SO_3^-$, $ClC_6H_4SO_3^-$, and boron anion represented by the formula (3).

The onium salt is preferably obtained by combining an onium salt having $S^+$ in the molecule with an onium salt having $I^+$ in the molecule in view of sensitivity and storage stability. In view of sensitivity and storage stability, the onium salt is preferably a polyvalent onium salt having at least two onium ion atoms in the molecule. At least two onium ion atoms in the cation are bonded through a covalent bond. Among polyvalent onium salts, those having at least two onium ion atoms in the molecule are preferable and those having $S^+$ and $I^+$ in the molecule are particularly preferable. Particularly preferable polyvalent onium salts are represented by the following formulas (6) and (7):

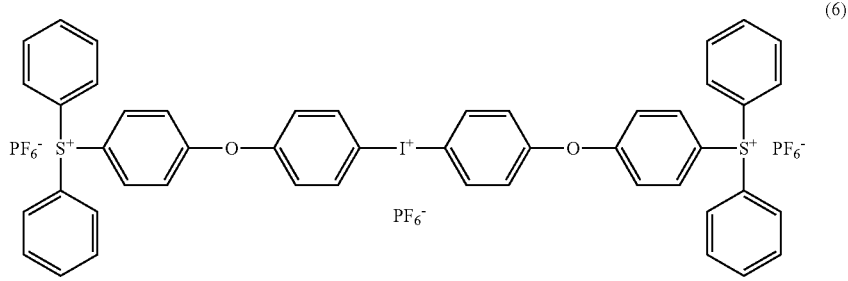

(6)

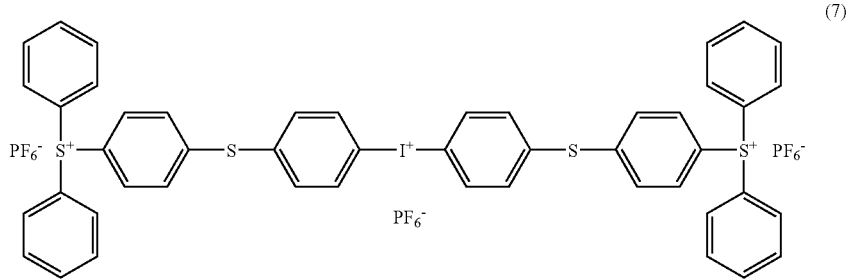

(7)

Furthermore, onium salts described in paragraphs [0033] to [0038] of the specification of Japanese Unexamined Patent Publication (Kokai) No. 2002-082429 can also be preferably used in the present invention.

The content of the onium salt is preferably within a range from 0.1 to 15% by weight, and particularly preferably from 0.5 to 7% by weight, based on the solid content of the photosensitive layer. When the content of the onium salt is less than 0.1% by weight, the resulting negative photosensitive lithographic printing plate may be insufficient in sensitivity and printing durability because of insufficient polymerization reaction. On the other hand, when the content of the onium salt is more than 15% by weight, the resulting negative photosensitive lithographic printing plate is inferior in developing properties. If necessary, at least two onium salts may be used in combination. Also the polyvalent onium salt may be used in combination with the monovalent onium salt.

The triazine-based compound is a known polymerization initiator which is used in the radical polymerization. For example, bis(trihalomethyl)-s-triazine can be preferably used as the photopolymerization initiator.

The amount of the triazine-based compound is usually a small amount. When the amount is too large, unpreferable results are obtained, that is, the triazine-based compound causes screening of the effective light and is crystallized and reprecipitated in the photosensitive layer after coating. The content of the triazine-based compound is preferably within a range from 0.1 to 15% by weight based on the solid content of the photosensitive layer. When the amount is within a range from 0.5 to 7% by weight, good results are obtained.

To the photopolymerization initiator, optional accelerators, for example, a mercapto compound such as mercapto-3-triazole, and an amine compound, may be added.

[Binder Resin]

When an alkalic developing solution is used, an organic high molecular weight polymer, which is soluble or swellable in alkalic water, is preferably used as a binder resin. Various polymers can be used as the organic high molecular weight polymer, which is soluble or swellable in alkalic water, and those having an alkali-soluble group (acid group) in the main chain or side chain are preferable. The acid group is preferably an acid group having pKa of 0 to 12, and carboxylic acid group, phenolic hydroxyl group, active amino and imino groups typified by sulfonamide group, N-sulfonyl carbamoyl group and N-acylcarbamoyl group are more preferable. Examples of the organic high molecular weight polymer include addition polymers having a carboxylic acid group in the side chain, for example, those described in publications such as Japanese Unexamined Patent Publication (Kokai) No. 59-44615, Japanese Examined Patent Publication (Kokoku) No. 54-34327, Japanese Examined Patent Publication (Kokoku) No. 58-12577, Japanese Examined Patent Publication (Kokoku) No. 54-25957, Japanese Unexamined Patent Publication (Kokai) No. 54-92723, Japanese Unexamined Patent Publication (Kokai) No. 59-53836 and Japanese Unexamined Patent Publication (Kokai) No. 59-71048, that is, methacrylic acid copolymer, acrylic acid copolymer, itaconic acid copolymer, crotonic acid copolymer, maleic acid copolymer and partially esterified maleic acid copolymer, acidic cellulose derivative having a carboxylic acid group in the side chain, those obtained by adding a cyclic anhydride to an addition polymer having a hydroxyl group, polyvinyl pyrrolidone, polyethylene oxide, alcohol soluble polyamide capable of increasing the strength of a cured film, and polyether of 2,2-bis-(4-hydroxyphenyl)-propane and epichlorohydrin. Among these, [benzyl(meth)acrylate/(meth)acrylic acid/optional other addition polymerizable vinyl monomer] copolymer and [allyl(meth)acrylate/(meth)acrylic acid/optional other addition polymerizable vinyl monomer] copolymer are particularly preferable. Polyurethane resins described in publications such as Japanese Examined Patent Publication (Kokoku) No. 7-120040, Japanese Examined Patent Publication (Kokoku) No. 7-120041, Japanese Examined Patent Publication (Kokoku) No. 7-120042, Japanese Examined Patent Publication (Kokoku) No. 8-12424, Japanese Unexamined Patent Publication (Kokai) No. 63-287944, Japanese Unexamined Patent Publication (Kokai) No. 63-287947, Japanese Unexamined Patent Publication (Kokai) No. 1-271741 and Japanese Unexamined Patent Publication (Kokai) No. 11-352691 can be used in applications of the present invention.

These high molecular weight polymers can improve the strength of the film made of the binder resin by introducing a radical reactive group into the side chain. Examples of the functional group capable of conducting the addition polymerization reaction include ethylenically unsaturated bond group, amino group and epoxy group, examples of the functional group capable of converting into a radical by irradiation with light include mercapto group, thiol group, halogen atom, triazine structure and onium salt structure, and examples of the polar group include carboxyl group and imide group. As the functional group capable of conducting the addition polymerization reaction, ethylenically unsaturated bond group such as acryl group, methacryl group, allyl group and styryl group are particularly preferable. It is also possible to use a functional group selected from an amino group, a hydroxy group, a phosphonic acid group, a phosphoric acid group, a carbamoyl group, an isocyanate group, an ureide group, an ureylene group, a sulfonic acid group and an ammonio group.

To maintain developing properties of a photosensitive lithographic printing plate, the binder resin to be used preferably has a proper molecular weight and acid value, and a high molecular weight polymer having an average molecular weight of 5,000 to 300,000 and an acid value of 20 to 200 (KOH mg/g-resin) is particularly preferable. These binder resins can be contained in the photosensitive layer in an optional amount. When the amount is more than 90% by weight, there may be obtained the results which are unpreferable in view of intensity of images formed by the layer. The amount is preferably from 10 to 90% by weight, and more preferably from 30 to 80% by weight. A weight ratio of the amount of the photopolymerizable compound to the binder resin is preferably adjusted within a range from 1/9 to 9/1, more preferably from 2/8 to 8/2, and most preferably from 3/7 to 7/3.

In case of an on-press developing type, in which the resulting printing plate is mounted on a press without being subjected to a development treatment after forming images and the non-image area of an original plate for printing is removed by supplying dampening water and an ink while rotating a cylinder, or of a high molecular weight polymer of a type of developing using a neutral developing solution after forming images, a graft polymer having an alkylene oxide chain in the side chain and a block copolymer having an alkylene oxide chain in the main chain are preferably used. As the alkylene oxide chain, a polyoxyethylene unit and a polyoxyethylene-polyoxypropylene unit are preferable. Examples thereof include a copolymer of polyethylene glycol monomethacrylate and the other unsaturated group-containing compound.

Examples of the graft polymer, which is preferably used herein, include those having both a hydrophilic alkylene oxide chain and a hydrophobic group in the side chain of the high molecular weight polymer. Examples of the hydrophobic group include a cyano group, a phenyl group, an amide group, a substituted phenyl group, an alkyl ester group and a substituted alkyl ester group. This substituted phenyl group includes those in which hydrogen of an aromatic ring is substituted or condensed with the other alkyl group, hetero atom, modifying group bonded to hetero atom, and plural aromatic rings. The substituted alkyl group itself may form a ring. The structure of the alkyl ester group is represented by the following formula.

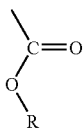

R is an alkyl or cycloalkyl group which may have a substituent. The side chain is bonded to the main chain of the binder via a carbonyl group (C=O).

The polyalkylene oxide chain, as used herein, means a polyalkylene oxide segment. In general, the major portion is composed of the polyalkylene oxide segment and also can have a linking group and an end group. The polyalkylene oxide segment refers to an oligomer or polymer containing a block of an alkylene oxide constituent unit.

The alkyleneoxide constituent unit is specifically a ($C_1$-$C_6$) alkylene oxide group and more specific examples thereof include a ($C_1$-$C_3$) alkylene oxide group.

Therefore, examples of the polyalkylene oxide segment include a linear or side chain alkylene oxide group having 1 to 3 carbon atom, such as —($CH_2$—O—), —($CH_2CH_2$—O—), —(CH($CH_3$)—O—), —($CH_2CH_2CH_2$—O—), —(CH($CH_3$)$CH_2$—O—), —($CH_2$CH($CH_3$)—O—), or a combination thereof. It is more preferable to have a —($CH_2CH_2$—O—) constituent unit. In the high molecular weight polymer, a number average molecular weight of the alkyleneoxide unit is preferably from 100 to 100,000, and particularly preferably from 500 to 10,000.

As the polyalkylene oxide chain, for example, the following are used.

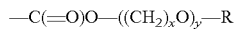

In the above formula, x represents an integer of 1 to 3, y represents 5 to 180, and R represents an end group. R is not limited, but is preferably a hydrogen atom or an alkyl group having 1 to 6 carbon atoms. Specific examples of the alkyl group include a methyl group, an ethyl group, an n-propyl group, an isopropyl group, an n-butyl group, a sec-butyl group, an isobutyl group, a t-butyl group, an n-pentyl group, an isopentyl group, a neo-pentyl group, an n-hexyl group, an isohexyl group, a 1,1-dimethylbutyl group, a 2,2-dimethylbutyl group, a cyclopentyl group and a cyclohexyl group.

Preferably, the polyalkylene oxide chain to be used has the following formula:

wherein y is from 12 to 200, and more preferably from 25 to 75. Still more preferably, y is from 40 to 50.

Examples of the copolymer component include a cyano group-containing monomer, an acrylate ester, a methacrylate ester, a styrene, a hydroxystyrene, acrylic acid and methacrylic acid. Preferable examples thereof include acrylonitrile, methacrylnitrile, acrylamide, methacrylamide, styrene and derivatives thereof, methyl methacrylate, and derivatives of allyl methacrylate.

One of specific examples of the binder resin is composed of the following copolymer components of a monomer and/or a macromer.

Copolymer component A): acrylonitrile, methacrylonitrile, or mixtures thereof.

Copolymer component B): poly(alkylene glycol)ester of acrylic acid or methacrylic acid, such as poly(ethylene glycol)methyl ether acrylate or poly(ethylene glycol)methyl ether methacrylate Copolymer component C): if necessary, a monomer such as styrene or methacrylamide, or mixtures of the monomers Copolymer component A): the content in the composition is preferably from 20 to 95%, and more preferably from 50 to 90%

Copolymer component B): the content in the composition is preferably from 1 to 40%, and more preferably from 4 to 30%

Copolymer component C): the content in the composition is preferably from 4 to 40%, and more preferably from 6 to 49%.

Examples of the macromer B of the copolymer component B) include polyethylene glycol monomethacrylate and polypropylene glycol methyl ether methacrylate, polyethylene glycol ethyl ether methacrylate, polyethylene glycol butyl ether methacrylate, polypropylene glycol hexyl ether methacrylate, polypropylene glycol octyl ether methacrylate, polyethylene glycol methyl ether acrylate, polyethylene glycol ethyl ether acrylate, polyethylene glycol phenyl ether acrylate, polypropylene glycol monoacrylate, polypropylene glycol monomethacrylate, polypropylene glycol methyl ether methacrylyrate, polypropylene glycol ethyl ether methacrylate, polypropylene glycol butyl ether methacrylate, polyethylene glycol/propylene glycol methyl ether methacrylate, poly(vinyl alcohol) monomethacrylate, polyvinyl alcohol monoacrylate, and mixtures thereof.

Examples of the copolymer component C include acrylic acid, methacrylic acid, acrylate ester, methacrylate ester such as methyl methacrylate, allyl methacrylate, hydroxyethyl methacrylate, styrene, hydroxystyrene, acrylamide, methacrylamide, and mixtures thereof. Among these, styrene, methacrylamide, and derivatives thereof are more preferable.

Specific examples thereof include styrene, 3-methylstyrene, 4-methylstyrene, 4-methoxystyrene, 4-acetoxystyrene, α-methylstyrene, acrylic acid, methyl acrylate, ethyl acrylate, butyl acrylate, n-hexyl acrylate, methacrylic acid, methyl methacrylate, ethyl methacrylate, n-propyl methacrylate, n-butyl methacrylic acid, n-pentyl methacrylate, neopentyl methacrylate, cyclohexyl methacrylate, n-hexyl methacrylate, 2-ethoxyethyl methacrylate, 3-methoxypropyl methacrylate, allyl methacrylate, vinyl acetate, vinyl butyrate, methyl vinyl ketone, butyl vinyl ketone, vinyl fluoride, vinyl chloride, vinyl bromide, maleic anhydride, maleimide, N-phenylmaleimide, N-cyclohexylmaleimide, N-benzylmaleimide, and mixtures thereof.

These monomers are synthesized by a known radical polymerization method. As a polymerization initiator, there can be preferably used known initiators such as azobisisobutyronitrile (AIBN).

As a solvent for radical polymerization, there can be used a liquid which is inert to the reacting materials and exerts no adverse influence on the reaction.

Specifically, there can be used esters such as ethyl acetate and butyl acetate; ketones such as methyl ethyl ketone, methyl isobutyl ketone, methyl propyl ketone and acetone; alcohols such as methanol, ethanol, isopropyl alcohol and butanol; ethers such as dioxane and tetrahydrofuran; and mixtures thereof.

In addition to the binder resin, at least one accessory binder resin may be contained. As the binder resin, a water-soluble or water-dispersible polymer is used. Examples thereof include cellulose derivatives such as carboxymethyl cellulose, methyl cellulose, hydroxypropylmethyl cellulose, hydroxypropylcellulose and hydroxyethyl cellulose; polyvinyl alcohol, polyacrylic acid, polymethacrylic acid, polyvinyl pyrrolidone, polylactide, polyvinylphosphonic acid, synthetic copolymer, and mixtures thereof. The synthetic copolymer refers to a copolymer of an alkoxypolyethylene glycol (meth)

acrylate such as methoxypolyethylene glycol (meth)acrylate, and a monomer such as (meth)methyl acrylate, butyl(meth)acrylate or allyl methacrylate.

In the photosensitive composition of the present invention, a small amount of a thermal polymerization inhibitor, to prevent unnecessary thermal polymerization of a photopolymerizable compound during the preparation or storage of the photosensitive composition, is added. Examples of this kind of the polymerization inhibitor include hydroquinone, p-methoxyphenol, di-t-butyl-p-cresol, pyrogallol, t-butyl catechol, benzoquinone, 4,4'-thiobis(3-methyl-6-t-butylphenol), 2,2'-methylenebis(4-methyl-6-t-butylphenol), N-nitrosophenylhydroxylamine primary cerium salt and N-nitrosophenylhydroxylamine aluminum salt. The amount of this kind of the thermal polymerization inhibitor is preferably from about 0.01 to 5% by weight based on the entire components of the photosensitive composition. If necessary, in order to prevent polymerization inhibition due to oxygen, higher fatty acid derivatives such as behenic acid and amide behenate may be added and distributed on the surface of the photopolymerizable photosensitive layer during the process of drying after coating. The amount of the higher fatty acid derivative is from 0.5 to 10% by weight based on the entire components of the photosensitive composition.

Furthermore, colorants may be added for the purpose of coloring the photosensitive composition. Examples of the colorant include dyes such as phthalocyanine-based pigments (for example, C.I. Pigment Blue 15:3, 15:4 and 15:6, etc.), azo-based pigments, carbon black and titanium oxide, Ethyl Violet, Crystal Violet, azo dyes, anthraquinone-based dyes and cyanine-based dyes. The amount of the dyes and the pigments is preferably from about 0.5 to 5% by weight based on the entire components of the photosensitive composition.

In order to improve physical properties of a cured film obtained from the photosensitive layer, additives, for example, inorganic fillers and plasticizers such as dioctyl phthalate, dimethyl phthalate and tricresyl phosphate may be added. For the purpose of improving coat properties of the coated surface, known surfactants may be added. Examples of the known surfactant include fluorine-based surfactants, polyoxyalkylene alkyl ether-based nonionic surfactants, and silicone-based surfactants such as dialkylsiloxane.

The photosensitive lithographic printing plate of the present invention comprises a substrate subjected optionally to various surface treatments, and the photosensitive layer made of the composition formed on the substrate. The photosensitive layer can be obtained by dissolving the photosensitive composition in various organic solvents and coating the resulting solution on the substrate. The photosensitive lithographic printing plate of the present invention is preferably a negative photosensitive lithographic printing plate.

Examples of the solvent, which can be used in the present invention, include acetone, methyl ethyl ketone, cyclohexane, ethyl acetate, ethylene dichloride, tetrahydrofuran, dimethyl ether, diethyl ether, toluene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycolethyl ether acetate, ethylene glycol monoisopropyl ether, ethylene glycol monobutyl ether acetate, 3-methoxy propanol, methoxymethoxy ethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethyl formamide, dimethyl sulfoxide, γ-butyrolactone, methyl lactate, ethyl lactate, methanol, ethanol, propanol, butanol and water. These solvents can be used alone or in combination. The solid content in the coating solution is preferably from 1 to 50% by weight.

The coating weight of the photosensitive layer the photosensitive lithographic printing plate of the present invention is preferably within a range from 0.1 to 10 $g/m^2$, more preferably from 0.3 to 5 $g/m^2$, and still more preferably from 0.5 to 3 $g/m^2$, in terms of a weight after coating and drying.

In the photosensitive lithographic printing plate of the present invention, a protective layer is preferably formed on the photosensitive layer so as to prevent exposure to air. The protective layer prevents penetration of oxygen existing in the air, which inhibits the polymerization reaction in the photosensitive layer, and prevents a low molecular weight compound such as basic substance penetrating into the photosensitive layer, and thereby make easier the plate exposure in an air. Therefore, the characteristics required of the protective layer include low permeability of a low molecular weight compound such as oxygen, good permeability of light used for exposure, excellent adhesion with the photosensitive layer and easy removal during a developing treatment.

As the material of the protective layer, for example, a water-soluble polymer compound having comparatively excellent crystallinity can be used, and specific examples thereof include water-soluble polymers such as polyvinyl alcohol, polyvinyl pyrrolidone, acidic celluloses, gelatin, gum arabic and polyacrylic acid. The use of polyvinyl alcohol among these polymers as a main component give good results to basic characteristics such as an oxygen screening property and a development eliminating property. Polyvinyl alcohol used in the protective layer may be partially substituted with an ester, an ether and an acetal as far as it can contain an unsubstituted vinyl alcohol unit for imparting required oxygen screening properties and water solubility. Further, a portion of the polyvinyl alcohol can contain the other copolymer component. Specific examples of polyvinyl alcohol (PVA) include those having a hydrolysis rate of 71 to 100% and a polymerization degree within a range from 300 to 2400. Specific examples thereof include PVA-105, PVA-110, PVA-117, PVA-117H, PVA-120, PVA-124, PVA-124H, PVA-CS, PVA-CST, PVA-HC, PVA-203, PVA-204, PVA-205, PVA-210, PVA-217, PVA-220, PVA-224, PVA-217EE, PVA-217E, PVA-220E, PVA-224E, PVA-405, PVA-420, PVA-613 and PVA-L8, which are manufactured by Kuraray Co., Ltd.

Components of the protective layer (selection of PVA and use of additives) and the coating weight are selected taking account of fog resistance, adhesion and scratch resistance, in addition to an oxygen screening property and a development eliminating property. The higher the hydrolysis rate of PVA to be used (the higher the content of an unsubstituted vinyl alcohol unit in the protective layer), the larger the thickness, the more the oxygen screening properties are enhanced, and thus it is advantageous in view of sensitivity. However, when oxygen screening properties are extremely enhanced, there arise problems that undesired polymerization reaction occurs during the production and storage and undesired fog and line pattern thickening occur during laser irradiation. Also adhesion with the image area and scratch resistance are very important in view of handling of the plate. That is, when a hydrophilic layer made of a water-soluble polymer is laminated on a hydrophilic polymer layer, film peeling due to poor adhesive force is likely to occur and the peeled portion causes defects such as poor film curing due to polymerization inhibition of oxygen. The method of improving adhesion between two layers includes a method of mixing a hydrophilic polymer composed mainly of polyvinyl alcohol with 20 to 60% by weight of am acrylic emulsion or a water-soluble vinyl pyrrolidone-vinyl acetate copolymer.

[Substrate]

The substrate of the photosensitive lithographic printing plate of the present invention is not specifically limited as far as the surface is hydrophilic, but it is preferably a dimensionally stable plate-shaped article. Examples of the substrate include paper, paper laminated with plastic (for example, polyethylene, polypropylene, polystyrene, etc.), plate made of metal such as aluminum (including aluminum alloy), zinc or steel, or an alloy thereof (for example, alloy with silicon, copper, manganese, magnesium, chromium, zinc, lead, bismuth, nickel, etc.), film made of plastic such as cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate or polyvinyl acetal, and paper or plastic film obtained by laminating or depositing the above metal or alloy thereon. Among these substrates, an aluminum plate is particularly preferable because of excellent dimensional stability and low price. Furthermore, a composite sheet comprising a polyethylene terephthalate film and an aluminum sheet bonded on the polyethylene terephthalate film, as described in Japanese Examined Patent Publication (Kokoku) No. 48-18327, is also preferable. The thickness is usually from about 0.05 to 1 mm.

In case of a substrate having the surface made of aluminum, the substrate is preferably subjected to a surface treatment such as a graining treatment, an anodizing treatment, or a treatment of dipping in an aqueous solution of sodium silicate, potassium fluorozirconate or a phosphate.

[Graining Treatment]

Examples of a graining treatment method include mechanical graining, chemical etching and electrolytic graining as disclosed in Japanese Unexamined Patent Publication (Kokai) No. 56-28893. Furthermore, there can be used an electrochemical graining method of electrochemically graining in a hydrochloric acid or nitric acid electrolytic solution, and a mechanical graining method such as wire brush graining method of scratching the surface of aluminum using a metal wire, or ball graining method of graining the surface of aluminum using an abrasive ball or an abrasive. These graining methods can be used alone or in combination. Among these methods, an electrochemical graining method of chemically graining in a hydrochloric acid or nitric acid electrolytic solution is useful in the present invention. In the electrochemical method, the preferable current density is within a range from 100 to 400 $C/dm^2$. More specifically, electrolysis is preferably conducted in an electrolytic solution containing 0.1 to 50% hydrochloric acid or nitric acid under the conditions of a temperature of 20 to 100° C., a time of 1 second to 30 minutes and a current density of 100 to 400 $C/dm^2$.

The aluminum substrate thus subjected to a graining treatment is chemically etched with an acid or an alkali. In case of using an acid as an etching agent, it requires a long time to break a fine structure and therefore it is disadvantageous in case of industrially applying the present invention. This problem is improved by using an alkali as an etching agent.

Examples of the alkali agent used preferably include sodium hydroxide, sodium carbonate, sodium aluminate, sodium metasilicate, sodium phosphate, potassium hydroxide and lithium hydroxide. The concentration and the temperature are within a range from 1 to 50%, and from 20 to 100° C., respectively, and the conditions are preferably selected so that the amount of aluminum dissolved is from 5 to 20 $g/m^3$.

After etching, pickling is conducted so as to remove stains (smuts) remained on the surface. Examples of the acid to be used include nitric acid, sulfuric acid, phosphoric acid, chromic acid, hydrofluoric acid and fluoroboric acid. Examples of the method for treatment of removing smuts after the electrochemical roughening treatment are preferably a method of contacting with 15 to 65 wt % sulfuric acid at a temperature of 50 to 90° C. as described in Japanese Unexamined Patent Publication (Kokai) No. 53-12739, and a method of alkali etching as described in Japanese Examined Patent Publication (Kokoku) No. 48-28123. In the present invention, the surface roughness (Ra) of the aluminum substrate is preferably from 0.3 to 0.7 μm.

[Anodizing Treatment]

The aluminum substrate thus treated is further subjected to an anodizing treatment. The anodizing treatment can be conducted by the method which has hitherto been used in this technical field. Specifically, when a direct current or an alternating current is applied to aluminum in an aqueous solution or a non-aqueous solution using sulfuric acid, phosphoric acid, chromic acid, oxalic acid, sulfamic acid and benzenesulfonic acid alone or in combination, an anodic oxide film is formed on the surface of aluminum. The conditions of the anodizing treatment vary depending on the electrolytic solution to be used and cannot be decided unqualifiedly, but are preferably as follows: the concentration of an electrolytic solution of 1 to 80%, a liquid temperature of 5 to 70° C., an electric current of 0.5 to 60 $ampere/dm^2$, a voltage of 1 to 100 V and an electrolysis time of 10 to 100 seconds.

Among these anodizing treatments, a method of anodizing in sulfuric acid at high electric current density described in the specification of British Patent No. 1,412,768 and a method of anodizing using an electrolytic bath containing phosphoric acid described in the specification of U.S. Pat. No. 3,511,661 are particularly preferable.

In the present invention, a coating weight of the anodic oxide film is preferably from 1 to 10 $g/m^2$. When the coating weight is less than 1 $g/m^2$, the plate is likely to be scratched. On the other hand, when the coating weight is more than 10 $g/m^2$, it is economically disadvantageous because a large amount of electric power is required in the production. The coating weight is preferably from 1.5 to 7 $g/m^2$, and more preferably from 2 to 5 $g/m^2$.

Furthermore, in the present invention, the substrate may be subjected to a sealing treatment after the graining treatment and the anodizing treatment. Such a sealing treatment is conducted by dipping a substrate in hot water or an aqueous solution containing an inorganic salt or an organic salt, or a steam bath. The substrate to be used in the present invention may be subjected to a treatment other than a silicate treatment using an alkali metal silicate, for example, a surface treatment such as treatment for dipping in an aqueous solution of potassium fluorozirconate or phosphate.

In the present invention, a photosensitive lithographic printing plate is produced by forming a photosensitive layer made of the above photosensitive composition on a substrate (in case of aluminum, aluminum subjected appropriately to the surface treatment is preferable) and optionally forming a protective layer. Before forming the photosensitive layer, an organic or inorganic under coat layer may be formed on the substrate, if necessary, or the substrate may be subjected to a sol-gel treatment in which a functional group capable of causing the addition reaction by a radical, as disclosed in Japanese Unexamined Patent Publication (Kokai) No. 7-159983.

Examples of the substance used to form the organic under coat layer include a water-soluble resin, for example, polyvinylphosphonic acid and a copolymer thereof, the polymer and the copolymer each having a sulfonic acid group in the side chain, polyacrylic acid, a water-soluble metal salt (for example, zinc borate), a yellow dye and an amine salt. More specifically, the organic compound used in the organic under-coat layer is selected from phosphonic acids having an amino group, such as carboxymethyl cellulose, dextrin, gum arabic and 2-aminoethylphosphonic acid; organic phosphonic acids such as phenylphosphonic acid, naphthylphosphonic acid, alkylphosphonic acid, glycerophosphonic acid, methylenediphosphonic acid and ethylenediphosphonic acid each may having a substituent; organic phosphoric acids such as phenylphosphoric acid, naphthylphosphoric acid, alkylphosphoric acid and glycerophosphoric acid each may having a substituent; organic phosphinic acids such as phenylphosphinic acid, naphthylphosphinic acid, alkylphosphinic acid and glycerophosphinic acid each may having a substituent; amino acids such as glycine and β-alanine; and hydrochlorates of amine having a hydroxyl group, such as hydrochlorate of triethanolamine. These organic compounds may be used in combination.

Particularly, a copolymer of vinylphosphonic acid and polyethylene glycol methacrylate is preferable. The weight average molecular weight of the polyethylene glycol moiety is particularly preferably from 80 to 400.

This organic under coat layer can be formed by the following method. That is, it is a method of dissolving the organic compound in water or an organic solvent such as methanol, ethanol or methyl ethyl ketone, or a solvent mixture to give a solution, coating the solution on a substrate, and drying the solution. Alternatively, it is a method of dissolving the organic compound in water or an organic solvent such as methanol, ethanol or methyl ethyl ketone, or a solvent mixture to give a solution, and dipping a substrate in the solution thereby to adsorb the organic compound to the substrate, followed by washing with water and further drying to form an organic under-coat layer.

In the former method, a solution containing 0.005 to 10% by weight of the organic compound can be coated by various methods. For example, any method such as bar coater coating, spin coating, spray coating or curtain coating method may be used. In the latter method, the concentration of the solution is from 0.01 to 20% by weight, and preferably from 0.05 to 5% by weight, the dipping temperature is from 20 to 90° C., and preferably from 25 to 50° C., and the dipping times is from 0.1 seconds to 20 minutes, and preferably from 2 seconds to 1 minute.

The solution can also be used at a pH within a range from 1 to 12 after adjusting the pH with a basic substance such as ammonia, trimethylamine or potassium hydroxide, or an acidic substance such as hydrochloric acid or phosphoric acid. Yellow pigments can also be added so as to improve tone reproducibility of the photosensitive lithographic printing plate.

The coating weight after drying of the organic under-coat layer is suitably from 2 to 200 mg/m$^2$, and preferably from 5 to 100 mg/m$^2$. When the coating weight is less than 2 mg/m$^2$, sufficient printing durability is not obtained. Even if the coating weight is more than 200 mg/m$^2$, printing durability does not vary.

Examples of the substance to be used in the inorganic under-coat layer include inorganic salts such as cobalt acetate, nickel acetate and potassium fluorotitanate. The method of forming the inorganic under-coat layer is the same as that described above.

The photosensitive lithographic printing plate thus obtained can be developed after directly exposed using an Ar laser, a second harmonic generation (SHG-LD, 350 to 600 nm) of a semiconductor laser, a YAG-SHG laser or an InGaN-based short wave semiconductor laser. In order to enable the photosensitive lithographic printing plate to be treated in daylight, a high-output laser having a maximum intensity within a near infrared or infrared range is preferably used. As the high-output laser having a maximum intensity within a near infrared or infrared range, various lasers having a maximum intensity within a near infrared or infrared range of 760 to 1200 nm can be used. For the purpose of enhancing the curing rate of the photopolymerizable photosensitive layer until development is conducted after imagewise exposure, a heating process at a temperature of 50 to 150° C. for 1 second to 5 minutes may be provided.

As the developing solution in the development treatment, conventionally known aqueous alkalic solutions can be used. Examples thereof include inorganic alkali agents such as sodium silicate, potassium silicate, sodium triphosphate, potassium triphosphate, ammonium triphosphate, sodium diphosphate, potassium diphosphate, ammonium diphosphate, sodium carbonate, potassium carbonate, ammonium carbonate, sodium hydrogen carbonate, potassium hydrogen carbonate, ammonium hydrogen carbonate, sodium borate, potassium borate, ammonium borate, sodium hydroxide, ammonium hydroxide, potassium hydroxide and lithium hydroxide. Also, organic alkali agents such as monomethylamine, dimethylamine, trimethylamine, monoethylamine, diethylamine, triethylamine, monoisopropylamine, diisopropylamine, triisopropylamine, n-butylamine, monoethanolamine, diethanolamine, triethanolamine, monoisopropanolamine, diisopropanolamine, ethyleneimine, ethylenediamine and pyridine may be used in combination. These alkali agents may be used alone or in combination.

Furthermore, the following other surfactants may be added to the developing solution. As the other surfactant, there can be used nonionic surfactants, for example, polyoxyethylene alkyl ethers such as polyoxyethylene lauryl ether, polyoxyethylene cetyl ether and polyoxyethylene stearyl ether, polyoxyethylene alkyl allyl ethers such as polyoxyethylene octyl phenyl ether and polyoxyethylene nonyl phenyl ether, polyoxyethylene alkyl esters such as polyoxyethylene stearate, and sorbitan alkyl esters such as sorbitan monolaurate, sorbitan monostearate, sorbitan distearate, sorbitan monooleate, sorbitan sesquioleate and sorbitan trioleate, monoglyceride alkyl esters such as glycerol monostearate and glycerol monooleate; anionic surfactants, for example, alkylbenzene sulfonates such as sodium dodecylbenzene sulfoate, alkylnaphthalene sulfonates such as sodium butylnaphthalene sulfonate, sodium pentylnaphthalene sulfonate, sodium hexylnaphthalene sulfonate and sodium octylnaphthalene sulfonate, alkyl sulfates such as sodium lauryl sulfate, alkyl sulfonates such as sodium dodecyl sulfonate, and sulfosuccinate ester salts such as sodium dilauryl sulfosuccinate; and amphoteric surfactants, for example, alkylbetains such as laurylbetain and stearylbetain and amino acids. Among these surfactants, anionic surfactants such as alkylnaphthalene sulfonates, alkylbetains, and nonionic surfactants having a polyoxyalkylene ether group represented by the formula (1):

$$R^1\text{—O—}(R^2\text{—O})_n H \qquad (1)$$

wherein $R^1$ represents an alkyl group having 3 to 15 carbon atoms which may have a substituent, an aromatic hydrocarbon group having 6 to 15 carbon atoms which may have a substituent, or a heterocyclic aromatic ring group having 4 to 15 carbon atoms which may have a substituent (examples of the substituent include an alkyl group having 1 to 20 carbon atoms, halogen atoms such as Br, Cl and I, an aromatic hydrocarbon group having 6 to 15 carbon atoms, an aralkyl group having 7 to 17 carbon atoms, an alkoxy group having 1 to 20 carbon atoms, an alkoxy-carbonyl group having 2 to 20 carbon atoms, and an acyl group having 2 to 15 carbon atoms), $R^2$ represents an alkylene group having 1 to 10 carbon atoms which may have a substituent (examples of the substituent include an alkyl group having 1 to 20 carbon atoms, and an aromatic hydrocarbon group having 6 to 15 carbon atoms), and n represents an integer of 1 to 100.

The $(R^2-O)_n$ moiety of the formula (1) may be two or three kinds of groups as far as it is within the above range. Specific examples thereof include a random or a block-shaped one composed of a combination of an ethyleneoxy group and a propyleneoxy group, a combination of an ethyleneoxy group and an isopropyloxy group, a combination of an ethyleneoxy group and a butyleneoxy group, or a combination of an ethyleneoxy group and an isobutylene group.

These surfactants may be used alone or in combination. The content of these surfactants in the developing solution is preferably from 0.1 to 20% by weight in terms of the active component.

In the present invention, the following components can be optionally used in combination, in addition to the above components. Examples thereof include organic carboxylic acids such as benzoic acid, phthalic acid, p-ethylbenzoic acid, p-n-propylbenzoic acid, p-isopropylbenzoic acid, p-n-butylbenzoic acid, p-t-butylbenzoic acid, p-2-hydroxyethylbenzoic acid, decanoic acid, salicylic acid and 3-hydroxy-2-naphthoic acid; and organic solvents such as isopropyl alcohol, benzyl alcohol, ethyl cellosolve, butyl cellosolve, phenyl cellosolve, propylene glycol and diacetone alcohol. In addition, chelating agents, reducing agents, dyes, pigments, water softeners, antiseptics and defoamers are exemplified.

The photosensitive lithographic printing plate of the present invention is developed with the developing solution is conducted at a temperature within a range from about 0 to 60° C., and preferably from about 15 to 40° C. according to a conventional method and, for example, the exposed lithographic printing plate is developed by rubbing with a brush while it is dipped in a developing solution. Furthermore, the development treatment may be conducted using an automatic processor. In that case, as the developing solution is exhausted according to the throughput rate, the throughput capacity may be recovered with a replenisher or a fresh developing solution. When the protective layer is formed on the photosensitive layer, removal of the protective layer and removal of the unexposed area of the photosensitive layer may be conducted simultaneously using the above developing solution. Alternatively, the unexposed area of the photosensitive layer may be removed after removing the protective layer with water or hot water. Water or hot water can contain the antiseptics described in Japanese Unexamined Patent Publication (Kokai) No. 10-10754 and organic solvents described in Japanese Unexamined Patent Publication (Kokai) No. 8-278636.

The photosensitive lithographic printing plate thus developed is preferably post-treated with washing water, a rinsing solution containing a surfactant, or a desensitizing solution containing gum arabic or a starch derivative, as described in publications such as Japanese Unexamined Patent Publication (Kokai) No. 54-8002, Japanese Unexamined Patent Publication (Kokai) No. 55-115045 and Japanese Unexamined Patent Publication (Kokai) No. 59-58431. These treatments can be used in combination in the post-treatment of the photosensitive lithographic printing plate of the present invention.

It is also possible to develop the plate with "water" with a pH in a neutral range taking account of recent environmental problems. Also in this case, it is possible to add the surfactant described in the surfactant, which can be used in the developing solution for the propose of improving developing properties, and the above desensitizing solution for the purpose of desensitizing the developed printing plate, to water as the developing solution.

Printing durability of the printing plate thus obtained by the above treatment can be improved by a well-known post exposure treatment or a heat treatment such as burning. Then, the lithographic printing plate obtained by the above treatment is used for printing many copies after mounting into an offset press.

The resulting photosensitive lithographic printing plate can also be used as a printing plate capable of initiating printing after the resulting photosensitive lithographic printing plate referred to as a on-press developing type one is imagewise exposed and mounted to a plate cylinder of the press, as it is.

EXAMPLES

The present invention will now be described in detail by way of examples, but the present invention is not limited to the scope of the following examples.

[Synthesis of Silane-Containing Monomer 1]

In a 100 ml flask, 22.27 g of polyethylene glycol monomethyl ether (Mn=550, manufactured by Aldrich Co.) was introduced. While stirring polyethylene glycol monomethyl ether using a mechanical stirrer, 10 g of 3-isocyanatepropyltriethoxysilane (A-1310, manufactured by Union Carbide Corporation) was introduced in the flask. After charging 3-isocyanatepropyltriethoxysilane, 0.5 g of dibutyltin dilaurate (manufactured by Tokyo Kasei Kogyo Co., Ltd.) was added. Since the temperature of the reaction mixture raised, the reaction mixture was cooled in a water bath. The reaction mixture was stirred overnight. After stirring, no residual isocyanate was confirmed by an IR spectrum. Then, 0.5 g of methanol was added and the contents were taken from the flask.

[Synthesis of Silane-Containing Monomer 2]

In a 100 ml flask, 20.73 g of polyethylene glycol monoacrylate (Mn=512, AE-400 manufactured by NOF CORPORATION) was introduced. While stirring polyethylene glycol monoacrylate using a mechanical stirrer, 10 g of 3-isocyanatepropyltriethoxysilane (A-1310, manufactured by Union Carbide Corporation) was introduced in the flask. After introducing 3-isocyanatepropyltriethoxysilane, 0.5 g of dibutyltin dilaurate (manufactured by Tokyo Kasei Kogyo Co., Ltd.) was added and, as the temperature of the reaction mixture raised, the reaction mixture was cooled in a water bath. The reaction mixture was stirred overnight. After stirring, no residual isocyanate was confirmed by an IR spectrum. Then, 0.5 g of methanol was added and the contents were taken from the flask.

[Synthesis of Silane-Containing Monomer 3]

In a 100 ml flask, 17.09 g of polyethylene glycol-polypropylene glycol monomethacrylate (BLEMMER 70PEP-350E, manufactured by NOF CORPORATION) and MEK were introduced. While stirring the mixture using a mechanical stirrer, 10 g of 3-isocyanatepropyltriethoxysilane (A-1310, manufactured by Union Carbide Corporation) was introduced in the flask. After introducing 3-isocyanatepropyltriethoxysilane, 0.5 g of dibutyltin dilaurate (manufactured by Tokyo Kasei Kogyo Co., Ltd.) was added. As the temperature of the reaction mixture raised, the reaction mixture was cooled in a water bath. The reaction mixture was stirred overnight. After stirring, no residual isocyanate was confirmed by an IR spectrum. Then, 0.5 g of methanol was added and the contents were taken from the flask.

[Synthesis of Silane-Containing Monomer 4]

In a 100 ml flask, while stirring a mixture of 15.0 g of a polyethylene glycol modified terminated diisocyanate compound (VPLS2306, manufactured by SUMIKA BAYER URETHANE CO., LTD.) and 15 g of MEK using a mechanical stirrer, 6.33 g of 3-aminopropyltriethoxysilane (KBM-903, manufactured by SHIN-ETSU CHEMICAL CO., LTD.) and 6.33 g of MEK were introduced in the flask. VPLS2306 is represented by the following formula.

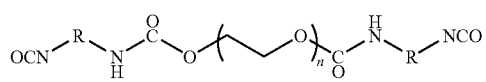

After introducing the 3-aminopropyltriethoxysilane mixture, stirring was conducted for 3 hours and 0.5 g of dibutyltin dilaurate (manufactured by Tokyo Kasei Kogyo Co., Ltd.) was added. Then, a mixture of 9.9 g of PETA and 9.9 g of MEK was added dropwise. The reaction mixture was stirred overnight. After stirring, no residual isocyanate was confirmed by an IR spectrum. Then, 0.5 g of methanol was added and the contents were taken from the flask. The resulting silane-containing monomer 4 is represented by the following formula.

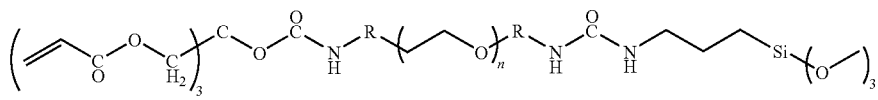

[Synthesis of Silane-Containing Monomer 5]

In a 100 ml flask, while mixing a mixture of 15.0 g of a polyethylene glycol modified terminated diisocyanate compound (VPLS2306, manufactured by SUMIKA BAYER URETHANE CO., LTD.) and 15 g of MEK using a mechanical stirrer, a mixture of 6.33 g 3-aminopropyltriethoxysilane (KBM-903, manufactured by SHIN-ETSU CHEMICAL CO., LTD.) and 6.33 g of MEK mixture was introduced into a flask. After introducing the 3-aminopropyltriethoxysilane mixture, stirring was conducted for 3 hours and 0.5 g of dibutyltin dilaurate (manufactured by Tokyo Kasei Kogyo Co., Ltd.) was added. Then, a mixture of 1.11 g of allyl alcohol (manufactured by Tokyo Kasei Kogyo Co., Ltd.) and 1.11 g of MEK was added dropwise. Allyl alcohol is represented by the following formula.

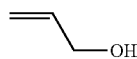

The reaction mixture was stirred overnight. After stirring, no residual isocyanate was confirmed by an IR spectrum. Then, 0.5 g of methanol was added and the contents were taken out from the flask. The resulting silane-containing monomer 5 is represented by the following formula.

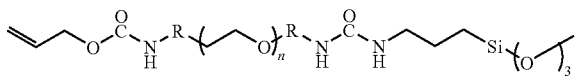

[Synthesis of Silane-Containing Monomer 6]

In a 100 ml flask, while stirring a mixture of 15.0 g of a polyethylene glycol modified terminated diisocyanate compound (VPLS2306, manufactured by SUMIKA BAYER URETHANE CO., LTD.) and 15 g of MEK using a mechanical stirrer, 6.33 g of a mixture of 3-aminopropyltriethoxysilane (KBM-903, manufactured by SHIN-ETSU CHEMICAL CO., LTD.) and 6.33 g of MEK was introduced in the flask. After introducing the 3-aminopropyltriethoxysilane mixture, stirring was conducted for 3 hours. Then, a mixture of 1.11 g of allylamine (manufactured by Tokyo Kasei Kogyo Co., Ltd.) and 1.11 g of MEK was added dropwise. Allylamine is represented by the following formula.

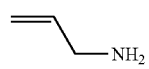

After stirring for 3 hours, 0.5 g of dibutyltin dilaurate (manufactured by Tokyo Kasei Kogyo Co., Ltd.) was added. The reaction mixture was stirred overnight. After stirring, no residual isocyanate was confirmed by an IR spectrum. Then, 0.5 g of methanol was added and the contents were taken out from the flask. The resulting silane-containing monomer 6 is represented by the following formula.

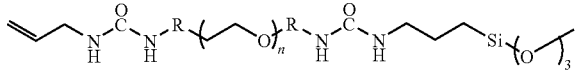

[Synthesis of Silica Compound 1]

5.15 g of silane-containing monomer 2 and 40 g of colloidal silica (MEK-ST) were introduced in a 200 ml flask. While stirring the mixture using a mechanical stirrer, the flask was heated to 80° C. After the temperature reached 80° C., 0.86 g of isopropyl alcohol (hereinafter referred to as "IPA") and 0.52 g of deionized water were added in the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 39.6% by weight.

[Synthesis of Silica Compound 2]

1.72 g of silane-containing monomer 1, 3.43 g of a silane-containing monomer 2 and 40 g of colloidal silica (MEK-ST) were introduced in a 200 ml flask. While stirring the mixture using a mechanical stirrer, the flask was heated to 80° C. After the temperature reached 80° C., 0.86 g of IPA and 0.52 g of deionized water were added in the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 40.3% by weight.

[Synthesis of Silica Compound 3]

3.43 g of silane-containing monomer 2 and 40 g of colloidal silica (MEK-ST) were introduced into a 200 ml flask. While stirring the mixture using a mechanical stirrer, the flask was heated to 80° C. After the temperature reached 80° C., 0.86 g of IPA and 0.52 g of deionized water were added in the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 38.1% by weight.

[Synthesis of Silica Compound 4]

1.72 g of silane-containing monomer 2 and 40 g of colloidal silica (MEK-ST) were introduced in a 200 ml flask. While stirring the mixture using a mechanical stirrer, the flask was heated to 80° C. After the temperature reached 80° C., 0.86 g of IPA and 0.52 g of deionized water were added in the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 35.3% by weight.

[Synthesis of Silica Compound 5]

5.15 g of silane-containing monomer 3 and 40 g of colloidal silica (MEK-ST) were introduced in a 200 ml flask. While stirring the mixture using a mechanical stirrer, the flask was heated to 80° C. After the temperature reached 80° C., 0.86 g of IPA and 0.52 g of deionized water were added in the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 40.4% by weight.

[Synthesis of Silica Compound 6]

5.15 g of silane-containing monomer 4 and 40 g of colloidal silica (MEK-ST) were introduced in a 200 ml flask. While stirring the mixture using a mechanical stirrer, the flask was heated to 80° C. After the temperature reached 80° C., 0.86 g of IPA and 0.52 g of deionized water were added in the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 39.9% by weight.

[Synthesis of Silica Compound 7]

5.15 g of silane-containing monomer 5 and 40 g of colloidal silica (MEK-ST) were introduced into a 200 ml flask. While stirring the mixture using a mechanical stirrer, the flask was heated to 80° C. After the temperature reached 80° C., 0.86 g of IPA and 0.52 g of deionized water were added to the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 39.9% by weight.

[Synthesis of Silica Compound 8]

5.15 g of silane-containing monomer 6 and 40 g of colloidal silica (MEK-ST) were introduced in a 200 ml flask. While stirring the mixture using a mechanical stirrer, the flask was heated to 80° C. After the temperature reached 80° C., 0.86 g of IPA and 0.52 g of deionized water were added in the flask. After 3 hours, 3.1 g of trimethyl orthoformate (manufactured by Tokyo Kasei Kogyo Co., Ltd.) was added, followed by stirring for one hour. After stirring, the contents were taken out from the flask. The nonvolatile content was 40.1% by weight.

[Synthesis of Urethane Acrylate 2]

46.5 g of N,N'-dimethyl acetamide (hereinafter referred to as "DMAC"), 28.65 g of hexamethylene diisocyanate buret type polyisocyanate (DESMODUR® N-3200, manufactured by Bayer Co.) and 3.48 g of 2-amino-4-hydroxy-6-methylpyrimidine (manufactured by Aldrich Co.) was introduced into a 300 ml four-necked flask equipped with a heating jacket, a temperature regulator, a mechanical stirrer, a condenser, a nitrogen gas introducing inlet and a pressure equalized funnel. The reaction mixture was slowly heated from about 87° C. to 90° C. and heating was maintained for 2 hours. The reaction proceeded and thus the reaction mixture gradually became transparent.

Then, the reaction mixture was cooled to 40° C. and a premixture of 82.1 g of DMAC, 11.92 g of PETA, 0.13 g of hydroquinone (manufactured by Tokyo Kasei Kogyo Co., Ltd.) and 0.1 g of dibutyltin dilaurate was added to the reaction mixture over 30 minutes. 0.1 g of dibutyltin dilaurate was further added and thus the temperature gradually raised to 60° C. The reaction mixture was cooled to 50° C. and 42.87 g of polyethylene glycol monoacrylate (Mn=512, AE-400 manufactured by NOF CORPORATION) and 0.1 g of dibutyltin dilaurate were added over 30 minutes. After 5 hours, residual isocyanate was not confirmed by an IR spectrum. The nonvolatile content was 40.0% by weight. The reaction mixture was a transparent liquid at room temperature.

Examples 1 to 8

On an aluminum substrate which was roughened by a brush, anodized with sulfuric acid and then post-treated with a polyethylene glycol methyl ether methacrylate-vinylphosphoric acid copolymer, each solution containing any one of silica compounds 1 to 8 described in Table 1 was coated so as to adjust a dry weight of the coat to 1.5 g/m². Specifically, each solution containing any one of silica compounds 1 to 8 was coated using a wire wound rod No. 26 and then dried in a conveyer oven, maintained at 100° C., for about 90 seconds.

TABLE 1

| Components | % by weight |
|---|---|
| Urethane acrylate 1[1] | 1.40 |
| Graft copolymer 1[2] | 2.88 |
| Urethane acrylate 2[3] | 0.70 |
| Irgacure 250[4] | 0.30 |
| Infrared absorbing dye[5] | 0.07 |
| Mercapt-3-triazole[6] | 0.14 |
| Byk 336[7] | 0.14 |
| Silica compound (30% solid content) | 0.95 |
| n-propanol | 46.66 |
| Water | 23.38 |
| Methyl ethyl ketone | 23.38 |
| to make | 100.00 |

[1] 80 wt % solution in 2-butanone, obtained by reacting DESMODUR N100 (aliphatic polyisocyanate resin based on hexamethylene diisocyanate, manufactured by Bayer Co.) with hydroxyethyl acrylate and pentaerythritol triacrylate
[2] 21% dispersion of an acrylonitrile/polyethylene glycol methyl ether methacrylate/styrene copolymer in a mixture of n-propanol/water (mixing rato: 80/20)
[3] 40 wt % solution in DMAC, obtained by reacting DESMODUR N3200 (aliphatic polyisocyanate resin based on hexamethylene diisocyanate, manufactured by Bayer Co.) with 2-amino-4-hydroxy-6-methylpyrimidine and polyethylene glycol monoacrylate (Mn = 512, AE-400 manufactured by NOF CORPORATION)
[4] 75% solution of iodonium(4-methoxyphenyl)[4-(2-methylpropyl)phenyl]hexafluorophosphoric acid) in propylene carbonate (manufactured by Ciba Speciality Chemicals Inc)
[5] dye of the above chemical formula (A)
[6] mercapt-3-triazole-1H,2,4 available from PCAS Co. (France)
[7] 25% solution of a modified dimethylpolysiloxane copolymer in a xylene/methoxypropylacetic acid solution (manufactured by Byk Chemie Co. (France))

Comparative Example 1

On an aluminum substrate which was roughened by a brush, anodized with sulfuric acid and then post-treated with a polyethylene glycol methyl ether methacrylate-vinylphosphoric acid copolymer, a solution containing colloidal silica MEK-ST in place of the silica compound described in Table 1 was coated so as to adjust a dry weight of the coat to 1.5 g/m$^2$. Specifically, a coating solution was coated using a wire wound rod No. 26 and then dried in a conveyer oven maintained at 100° C. for about 90 seconds.

Comparative Example 2

On an aluminum substrate which was roughened by a brush, anodized with sulfuric acid and then post-treated with a polyethylene glycol methyl ether methacrylate-vinylphosphoric acid copolymer, a solution containing no silica compound described in Table 1 was coated so as to adjust a dry weight of the coat to 1.5 g/m$^2$. Specifically, a coating solution was coated using a wire wound rod No. 26 and then dried in a conveyer oven maintained at 100° C. for about 90 seconds.

Comparative Example 3

5.15 g of silane-containing monomer 1, 40 g of colloidal silica (MEK-ST manufactured by NISSAN CHEMICAL INDUSTRIES, LTD., 30% solid MEK solution of particles having a particle size of 10 to 20 nm) were introduced in a 200 ml flask. While stirring the mixture using a mechanical stirrer, the flask was heated to 80° C. After the temperature reached 80° C., 0.86 g of IPA and 0.52 g of demineralized water were added in the flask. After 3 hours, 3.1 g of trimethyl orthoformate (manufactured by Tokyo Kasei Kogyo Co., Ltd.) was added, followed by stirring for one hour. After stirring, contents were taken out from the flask. The nonvolatile content was 39.4% by weight (hereinafter referred to as a "comparative silica compound").

On an aluminum substrate which was roughened by a brush, anodized with sulfuric acid and then post-treated with a polyethylene glycol methyl ether methacrylate-vinylphosphoric acid copolymer, a solution containing the above comparative silica compound in place of the silica compound described in Table 1 was coated so as to adjust a dry weight of the coat to 1.5 g/m$^2$. Specifically, a coating solution was coated using a wire wound rod No. 26 and then dried in a conveyer oven, maintained at 100° C., for about 90 seconds.

RESULTS

With respect to the photosensitive lithographic printing plates obtained in Examples 1 to 8 and Comparative Examples 1 to 3, the degree of adhesion of the photosensitive layer to the substrate and ink sediments characteristics during printing were evaluated. The results are shown in Table 2. Images were formed by using a CREO Trendsetter 3244 under the conditions of a drum speed of 90 rpm and a setting power of 10 W (225 mJ/cm$^2$). Tests on above respective characteristics were conducted by applying ink by hand work in a laboratory. The lithographic printing plate with images formed thereon was washed with dampening water containing 1% IPA and 1% NA-108W (etching solution, manufactured by Dainippon Ink and Chemcials, Incorporated) and a portion thereof was rubbed with a cloth impregnated with an ink once, twice, three times, five time and twenty times. Then, the wetted non-image area was slowly rubbed with a cloth impregnated with an ink. In some lithographic printing plates, the ink was not transferred to the non-image area. In that case, it was evaluated that those lithographic printing plate are excellent in ink scumming resistance. The mage area was also rubbed so as to evaluate the adhesion degree. The adhesion degree was evaluated by damage of the image area caused by rubbing.

Furthermore, a printing test was conducted using the plates obtained in Examples 1 to 8 and Comparative Examples 1 to 3. In a printing test, Komori S-26 and Roland R-200 were used as a press, DIC GEOS-GN Grade was used as an ink, Royal Coat 44.5 kg/A manufactured by Oji Paper Co., Ltd. was used as a printing paper, an aqueous solution containing 1% DIC K-705 and 10% IPA and an aqueous solution containing 1% DIC NA-108W and 1% IPA were used as dampening water, and (Kinyo) S-7400 manufactured by Kinyosha Co., Ltd. was used as a blanket, respectively. An accelerated print run length test was conducted using a Komori S-26. As a result, the solid image area was damaged with time. When the paper is damaged, it is regarded as the end of the print raw length. This printing test was repeated 6000 times. In the printability test using a Roland R-200, the non-image area of the plate should be developed after 10 rotations of a dampening water roll and the image area should receive sufficient amount of the ink after sheet printing 30 times. If these characteristics are not impaired by the printing test, printability is rated as "pass".

As is apparent from the results shown in Table 2, evaluation results of the adhesion degree in the laboratory have a correlation with print run length in the printing test and also the evaluation results of the ink scumming resistance in the laboratory have a correlation with printability in the printing test.

TABLE 2

| | | Evaluation | | Printing test | |
|---|---|---|---|---|---|
| | Photosensitive lithographic printing plate Silica surface treatment | Adhesion degree | Ink scumming resistance | Print run length | Printability |
| Example 1 (silica compound 1) | PEG/acrylate | A | A | 6000 | Excellent |
| Example 2 (silica compound 2) | PEG + PEG/acrylate | A | A | 6000 | Excellent |
| Example 3 (silica compound 3) | PEG/acrylate reduce 1 | B | A | 4000 | Excellent |
| Example 4 (silica compound 4) | PEG/acrylate reduce 2 | C | B | 3000 | Excellent or Good |
| Example 5 (silica compound 5) | PEG/PPG methacrylate | A | A | 6000 | Excellent |
| Example 6 (silica compound 6) | PEG/PETA | B | A | 4000 | Excellent |

TABLE 2-continued

|  | Photosensitive lithographic printing plate Silica surface treatment | Evaluation | | Printing test | |
|---|---|---|---|---|---|
| | | Adhesion degree | Ink scumming resistance | Print run length | Printability |
| Example 7 (silica compound 7) | PEG/allyl | B | A | 4000 | Excellent |
| Example 8 (silica compound 8) | PEG/allyl | B | A | 4000 | Excellent |
| Comparative Example 1 | No functional group | D | D | 500 | Poor |
| Comparative Example 2 | No. silica sol | E | A | 300 | Good |
| Comparative Example 3 (Comparative silica compound) | PEG | D | A | 500 | Good |

The invention claimed is:

1. A photosensitive composition comprising:
   modified silica particles the surfaces of which are modified by an organic compound having at least one ethylenically unsaturated group, at least one hydrophilic moiety and at least one silyloxy group that is reacted with hydroxyl groups on the silica particle surface to form covalent bonds and thereby leaving the ethylenically unsaturated groups as reactive sites,
   an infrared absorber,
   a photopolymerization initiator that provide free radicals, and
   a free radical photopolymerizable compound,
   wherein the infrared absorber is represented by $D^+A^-$ wherein $D^+$ represents a cationic dye having an absorption in the range of from 760 nm to 1200 nm and $A^-$ represents an anion.

2. The composition of claim 1 wherein the hydrophilic moiety is a polyoxyalkylene chain.

3. The composition of claim 1 wherein the ethylenically unsaturated group and the silyloxy group are located at either end of the molecular chain of the organic compound.

4. The composition of claim 1 wherein the organic compound is represented by the following formula:

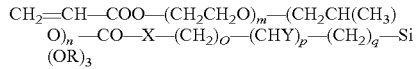

group), Y represents a $C_1$-$C_6$ alkyl group or a halogen atom, m represents an integer of 0 to 100, n represents an integer of 0 to 100, provided that m+n represents 1 or more,
o represents an integer of 0 to 10, p represents an integer of 0 to 5, and
q represents an integer of 0 to 10, provided that o+q represents 1 or more.

5. The composition of claim 1 wherein the modified silica particles have a size of from 1 to 100 nm.

6. The composition of claim 1 wherein the modification rate of the surface of the modified silica particles is from 50 to 99%.

7. The composition of claim 1 further comprising a binder resin.

8. The composition of claim 1 wherein the photopolymerization initiator is an organic boron compound, onium salt, or triazine compound.

9. The composition of claim 7 wherein the binder resin is a graft polymer having side chains containing an alkylene oxide, or a block copolymer having an alkylene oxide in the main chain.

10. A photosensitive negative-working lithographic printing plate precursor comprising a substrate, and having thereon a photosensitive layer comprising the photosensitive composition of claim 1, and
    said printing plate precursor optionally having a protective layer on the photosensitive layer.

11. The printing plate precursor of claim 10 wherein the hydrophilic moiety of the organic compound on the modified silica particles is a polyoxyalkylene chain.

12. The printing plate precursor of claim 10 wherein the ethylenically unsaturated group and the silyloxy group are located at either end of the molecular chain of the organic compound on the modified silica particles, and the modified silica particles have a size of from 1 to 100 nm.

13. The printing plate precursor of claim 10 wherein the organic compound on the modified silica particles is represented by the following formula:

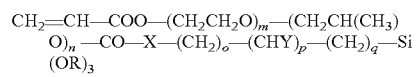

wherein R represents a $C_1$-$C_6$ alkyl group, X represents a divalent organic group selected from —$CH_2$—, —O—, —S— and —NZ— (wherein Z represents H or a $C_1$-$C_6$ alkyl group), Y represents a $C_1$-$C_6$ alkyl group or a halogen atom, m represents an integer of 0 to 100, n represents an integer of 0 to 100, provided that m+n represents 1 or more,
o represents an integer of 0 to 10, p represents an integer of 0 to 5, and
q represents an integer of 0 to 10, provided that o+q represents 1 or more.

14. The printing plate precursor of claim 10 wherein said photosensitive layer further comprises a binder resin.

15. The printing plate precursor of claim 10 wherein the infrared absorber in the photosensitive layer is represented by $D^+A^-$ wherein $D^+$ represents a cationic dye having an absorption in the range of from 760 nm to 1200 nm and $A^-$ represents an anion, and the photopolymerization initiator is an organic boron compound, onium salt, or triazine compound.

16. The printing plate precursor of claim 14 wherein the binder resin is a graft polymer having side chains containing an alkylene oxide, or a block copolymer having an alkylene oxide in the main chain.

17. A method of preparing a lithographic printing plate comprising:
    A) imagewise exposed the lithographic printing plate precursor of claim 10 that has a hydrophilic substrate, to imaging radiation to provide exposed and non-exposed regions, and B) with or without a heating process after imagewise exposure, removing the non-exposed regions.

18. The method of claim 17 wherein imagewise exposure carried out using infrared radiation.

19. The method of claim 17 wherein the non-exposed regions are removed during on-press development.

20. The method of claim 17 wherein the non-exposed regions are removed using an alkaline developer, water, or hot water in off-press development.

* * * * *